United States Patent [19]

Versteeg

[11] 4,083,798

[45] Apr. 11, 1978

[54] STABILIZED STATIC LIQUID MEMBRANE COMPOSITIONS

[75] Inventor: Joseph Versteeg, Roselle, N.J.

[73] Assignee: Exxon Research & Engineering Co., Linden, N.J.

[21] Appl. No.: 697,149

[22] Filed: Jun. 17, 1976

[51] Int. Cl.$^2$ ............................................. B01J 13/00
[52] U.S. Cl. .................................... 252/312; 252/314; 252/522; 424/19
[58] Field of Search .......................... 252/312; 424/168

[56] References Cited

U.S. PATENT DOCUMENTS

| | | | |
|---|---|---|---|
| 1,440,356 | 12/1922 | Morrell | 252/311.5 |
| 1,914,902 | 6/1933 | Volck | 252/312 X |
| 3,399,263 | 8/1968 | Strazdins et al. | 424/86 X |

Primary Examiner—Richard D. Lovering
Attorney, Agent, or Firm—Robert J. Baran; Ernest A. Forzano

[57] ABSTRACT

The instant invention relates to novel compositions, methods for their preparation and the use of said compositions for the purposes of slow or controlled release of active ingredients such as fragrances and pharmaceuticals. These novel compositions are prepared by dispersing an aqueous phase into an oil to form a first emulsion. This first emulsion is then dispersed as droplets in a second aqueous phase in the presence of a water soluble protein and a gelling polysaccharide. These novel compositions are characterized as stable to layering and coalescence of the droplets of the first emulsion while retaining pourability. In the internal phase of the droplets of the first emulsion active ingredients such as fragrances and pharmaceuticals may be retained and can be released either over a long period of time by permeation due to the solubility of said active ingredients in the external phase of the first emulsion or can be retained indefinitely until the first emulsion is broken to release instantaneously the active ingredients.

7 Claims, No Drawings

STABILIZED STATIC LIQUID MEMBRANE COMPOSITIONS

FIELD OF THE INVENTION

The instant invention relates to novel compositions, methods for their preparation and the use of said compositions for the purposes of slow or controlled release of active ingredients such as fragrances and pharmaceuticals. These novel compositions are prepared by dispersing an aqueous phase into an oil to form a first emulsion. This first emulsion is then dispersed as droplets in a second aqueous phase in the presence of a water soluble protein and a gelling polysaccharide. These novel compositions are characterized as stable to layering and coalescence of the droplets of the first emulsion while retaining pourability. In the internal phase of the droplets of the first emulsion active ingredients such as fragrances and pharmaceuticals may be retained and can be released either over a long period of time by permeation due to the solubility of said active ingredients in the external phase of the first emulsion or can be retained indefinitely until the first emulsion is broken to release instantaneously the active ingredients.

BACKGROUND OF THE PRIOR ART

The use of the liquid membrane technology, for example, see U.S. Pat. No. 3,779,907, in the preparation of products wherein the liquid membrane acts as a barrier for the release of an active ingredient is disclosed in U.S. Ser. No. 271,398, filed July 13, 1972, and U.S. Ser. No. 293,028, filed Sept. 28, 1972, herein incorporated by reference. These materials while suitable for the purposes disclosed in these patent applications suffer from one disadvantage, that is since the compositions are three phase emulsions, i.e., multiple emulsions, they have limited stability. After a period of time which in some instances may be less than minutes these materials separate into an emulsion phase, that is the desired structure of the compositions, i.e. emulsion droplets suspended in a continuous phase, is lost and the emulsion droplets coalesce and form a continuous emulsion either floating on or beneath the original continuous phase. One method which has been disclosed in these patent applications for improving the stability of the desirable multiple emulsion structure comprises adjusting the specific gravity of the continuous phase and the emulsion droplets so that they are equivalent. It will readily be appreciated by those skilled in the art that this is difficult and in certain cases impossible.

The compositions of this invention are characterized as stable multiple emulsions. These compositions are further characterized as pourable although in some variations the system may be gelled. Gelled systems however are not desirable.

Various other workers in the art have used multiple emulsions in processes for preparing emulsions encapsulated in solid capsules. During the preparation of this encapsulated emulsion, a three phase emulsion, i.e., a multiple emulsion, exists which comprises droplets of emulsion suspended in a continuous phase. This system however only exists while under the influence of agitation. for the purposes of the invention disclosed in these patents, this is sufficient since the continuous phase and/or the interface of the external phase of the emulsion and said continuous phase is converted into a solid capsule. Thus when agitation is terminated solid capsules are obtained. The instant compositions differ from the compositions taught therein in that solid capsules are not desired nor obtained.

SUMMARY OF THE INVENTION

The instant invention relates to methods for making stable multiple emulsions, the emulsions, and the uses thereof. The stable multiple emulsions of the instant invention are characterized as preferably being pourable.

The instant invention may best be understood with reference to the method for making the novel compositions disclosed herein. In preparing the novel compositions of the instant invention a first emulsion is prepared by means known in the art. This first emulsion is a water-in-oil emulsion, that is the internal phase of the emulsion is an aqueous solution while the external phase of the emulsion is immiscible with water. The internal phase of this emulsion comprises an active ingredient which may be a fragrance or pharmaceutical. Normally, the active ingredient is either insoluble in the oil phase of the emulsion or soluble to the extent of less than 0.5 weight percent at 25° C. This first emulsion is formed by methods known in the art, for example, an aqueous solution is mixed with an aqueous immiscible solution, i.e., an oil, under conditions of agitation and preferably in the presence of surfactants. The ratio of volume of the aqueous phase to the volume of the oil phase may vary from 1/10 to 1/1, preferably from 1/3 to 1/2. Agitation is provided at sufficient shear rates to disperse the aqueous phase into droplets and form stable emulsions. The surfactants, for example, the surfactants disclosed in U.S. Pat. No. 3,779,907 above are added in the amount necessary to provide stability to this first emulsion.

The first emulsion is then dispersed as droplets in a second aqueous solution. This second aqueous solution, which may be designated as the continuous phase of the instant novel compositions, contains a water solubilized protein and a gelling polysaccharide. Note that throughout this specification the term "water solubilized protein" includes proteins which are naturally soluble in aqueous solutions or modified, e.g., by partial hydrolysis, digestion, etc., to be soluble in aqueous solutions. "Gelling polysaccharides" are polysaccharides such as agar, pectin, starch, which can be dissolved in hot water and form gelled solutions when cooled. It is this combination which is critical to obtain th desired compositions of the instant invention. The first emulsion is added to the aqueous solution under conditions of relatively mild agitation. Water solubilized protein may be provided in aqueous external solutions prior to the addition of the first emulsion or concurrently. The same may be said of the gelling polysaccharide. Generally it is preferable to avoid gelling of the polysaccharide solution. This is accomplished by solubilizing the gel at elevated temperature, cooling slightly below the gelling point and before it has time to set up (usually limited to less than 15 minutes), then adding premade and premeasured water solubilized protein. The water solubilized protein is preferably made up ahead of time since it is stable for at least several days. Some particulate debris may appear after this time which is undesirable but not critical to the effect of this invention. The gelling polysaccharide is preferably made up as required and used warm (after solubilizing at higher temperature) to prevent gelling. It can however be made up in advance and when required for use degelled by heating and then cooled until warm (about 95° F in the examples below). The amount of the protein and the polysaccharide is sufficient to provide stable multiple emulsions, but preferably insufficient to gel the continuous phase. For example, the amounts may vary from 1 to 4 weight % of the aqueous external phase with the polysaccharide the most critical since concentrations are preferred where rapid gelation is avoided (e.g., 1 to 2 weight % for agar). In general, the ratio of protein to polysaccharide will vary from 1/2 to 1/1 by weight. The ratio of the volume of the first emulsion to the volume of the continuous phase of the multiple emulsion will vary from 1.5 to 2.6, preferably 2.0 to 2.5. It will be recognized that the theoretical closest packing of spheres is represented by a ratio of 2.8. Experimental attempts to use this or a higher ratio failed to develop stable products apparently because of the stress of sphere distortion. During their short life it was observed that spheres were distorted into crude polyhedra. It is noted that the novel compositions will remain pourable and to some extent sprayable over the various preferred amounts disclosed herein, i.e., these compositions can flow through the orifice of a container at a temperature range of from 40° to 100° F. This desirable result allows the preparation of compositions wherein the external phase of the first emulsion can act as a membrane while said first emulsion remains as suspended droplets which do not coalesce upon standing.

The advantages of the instant compositions over the compositions disclosed in U.S. Ser. No. 293,028 fied Sept. 28, 1972, and 271,398, filed July 13, 1972, are derived from the fact that they are container storable in a homogeneous state until use. The advantages over solid microencapsulation systems are that the whole system may be prepared in a fluid mix and used as such without requiring hardening, separation from fluid, etc., as required for solid encapsulation.

The instant compositions have special advantage in pesticide use, i.e., where the active ingredient is a pesticide. The spheres of the first emulsion are very narrow in size distribution and when the instant compositions are used as a coarse spray the outer aqueous phase will evaporate leaving the individual spheres of said first emulsion. The droplets of the compositions remaining after spraying are therefore limited to the minimum size of the individual sphere. These are much larger than the smaller sizes in conventional spraying. The smaller particle sizes in conventional spraying cause unwanted drifting well beyond the target area (frequently several miles) and this drift is avoided by the high lower limit of particle size in the compositions of this invention. Pesticide contamination of nontarget areas would therefore be avoided.

The system's storability of the instant compositions provides the opportunity for making products which slowly release their active ingredient and can also be shipped, distributed and dispersed from containers by pouring or coarse spraying. They are therefore useful for drugs which are ingested (easily taken as a fluid with slow release in the stomach and intestines), fragrances applied to the skin or other surfaces, pesticides, air freshener and other products where slow release is desirable.

The instant compositions also have the advantage of high adhesion to surfaces which they wet. The distribution over a target area is therefore contained to that target area.

A further advantage of the instant compositions is that more rapid release of the active ingredient may be obtained after application, if this is desirable, simply by use of low energy mechanical rubbing. This destroys the spheres and increases release since the system then adheres to the surface as a thin film.

The active ingredient which may be present in the aqueous phase of the first emulsion may be selected from those known in the art. For example, see the list of compositions disclosed in the above patent applications.

The following are specific embodiments of the instant invention, however, there is no intention to be limited to these embodiments other than by the limitations in the claims.

EXAMPLE 1

A multiple emulsion was made by emulsifying 29% ammonia in $H_2O$ in an oil consisting of 2% Span 80[A], 4% polyamine[B] and 94% Solvent 600 Neutral[C]. This emulsion was then dispersed in water at a ratio of 1 part emulsion to two parts water with slow stirring (100 rpm). After 30 minutes the stirring was stopped. The times for the emulsion to separate and coalesce was 1 minute.

[A]Sorbitan monooleate available from Atlas Chemical
[B]See the formula given in Example 2 of U.S. Pat. No. 3,779,907
[C]A paraffinic oil available from Exxon Chemical

EXAMPLE 2

The procedure of Example 1 was followed but the external water phase was modified as follows: 1% agar was added to the water phase and heated to 180° F. to dissolve it. It was then cooled to 95° F. Stirring was continued while the multiple emulsion was made as in Example 1. The multiple emulsion was poured into a Petri dish at 73° F. The system quickly gelled and stabilized the dispersion. The system was stable for 48 hours but was not pourable after cooling to 73° F.

EXAMPLE 3

A multiple emulsion was made by dissolving 8% sodium salicylate and 8% sucrose in water and then emulsifying the aqueous solution in an oil consisting of 2% Span 80[A], 0.5% polyamine[B], 3.5% polyisobutylene and 94% Solvent 100 Neutral[C]. The emulsion was dispersed in a water solution of 0.8% egg albumin. The water of solution had previously had dissolved in it 0.5% NaCl and 0.4% $NaHCO_3$ to solubilize the albumin. Dispersion was by slow stirring for four 8-hour periods. When agitation was stopped the dispersion formed a layer on top but the dispersed spheres retained their shape and identity for more than 2 weeks.

EXAMPLE 4

A liquid membrane system was made by emulsifying 29% aqueous ammonia in a surfactant system (oil) of 2% Span 80[A], 19% polyamine[B], 10% polyisobutylene and 69% Solvent 600 Neutral[C]. An external aqueous phase was made in two parts. 1.6% egg albumin was dissolved in water which had previously had 1.0% NaCl and 0.8% $NaHCO_3$ dissolved in it. A second aqueous solution of 2% agar in water was made by heating to 180° F and then cooling to 115° F. The two aqueous solutions were combined to provide an external phase at 95° F. The emulsion was then dispersed in the external phase with slow agitation in a ratio of 2/1 of emulsion-/external aqueous phase. The resulting dispersion on standing without agitation showed no coalescence or layering in 20 days. The dispersed spheres were clearly visible as such under low power magnification. Previous experience with Example 3 would indicate that the stability will continue indefinitely. The system poured easily. A slight tendency towards instability can be induced by very low shear (hand bottle rotation) and 5 to 10% of the aqueous phase appears as a bottom layer. This disappears and the original stability returns on vigorous shaking.

EXAMPLE 5

A product was made according to Example 4 and sprayability of the product was determined using as a criterion the survival of the dispersed spheres (non-coalescence after impingement on an aluminum foil target. The results indicate that the spraying orifice needs to be 3 mm or larger to obtain over 50% survival as shown below.

| Sprayer | Driving Force | Orifice Size mm | Spray Pattern | % of Spheres Surviving[1] |
|---|---|---|---|---|
| Seltzer Bottle | $CO_2$ Cartridge | 10 | Stream | 100 |
| Polyethylene Wash Bottle | Hand Squeezing | 3 | Stream | 65 |
| Polyethylene Wash Bottle | Hand Squeezing | 1.8 | Stream | 35 |
| Polyethylene Wash Bottle | Hand Squeezing | 1.6 | Stream | 33 |
| Polyethylene Wash Bottle | Hand Squeezing | 1.1 | Stream | 35 |
| Hydraulic Hand Sprayer | Hand Pump | 0.5 | Coarse Spray | 0 |

[1]By visual examination at 2X magnification

What is claimed is:

1. A pourable composition stable to layering and coalescence which comprises a water-in-oil emulsion, wherein the internal phase of said emulsion is an aqueous solution containing an active ingredient, the volumetric ratio of said internal phase to said oil phase ranges from 1/10 to 1/1, said emulsion is dispersed as droplets in a continuous aqueous phase which contains 1-4 weight % of a water-soluble protein and 1-4 weight % of a gelling polysaccharide, wherein the ratio of said protein to said polysaccharide ranges from 1/2 to 1/1 by weight, and the volumetric ratio of said water-in-oil emulsion to said continuous phase ranges from 1.5-2.6.

2. The composition of claim 1 wherein said active ingredient is soluble in said oil phase of said emulsion to the extent of less than 0.5 weight percent at 25° C.

3. The composition of claim 1, wherein the volumetric ratio of said internal phase to said oil phase ranges from 1/3 to 1/2.

4. The composition of claim 1 wherein the volumetric ratio of said water-in-oil emulsion to said continuous phase ranges from 2.0-2.5.

5. The composition of claim 1 wherein said water-soluble protein is albumin.

6. A pourable composition stable to layering and coalescence which comprises a water-in-oil emulsion, wherein the internal phase of said emulsion is an aqueous solution containing an active ingredient, the volumetric ratio of said internal phase to said oil phase ranges from 1/10 to 1/1, said emulsion is dispersed as droplets in a continuous aqueous phase which contains 1-4 weight % of a water-soluble protein and 1-4 weight % agar, wherein the ratio of said protein to agar ranges from 1/2 to 1/1 by weight, and the volumetric ratio of said water-in-oil emulsion to said continuous phase ranges from 1.5-2.6.

7. The composition of claim 6 wherein the concentration of said agar in said continuous aqueous phase ranges from 1-2 weight percent.

* * * * *